(12) United States Patent
De La Rama et al.

(10) Patent No.: US 11,419,675 B2
(45) Date of Patent: Aug. 23, 2022

(54) ABLATION CATHETER HAVING FLEXIBLE TIP WITH MULTIPLE FLEXIBLE ELECTRODE SEGMENTS

(71) Applicant: ST. JUDE MEDICAL, LLC, Abbott Park, IL (US)

(72) Inventors: Alan De La Rama, Cerritos, CA (US); Cary Hata, Irvine, CA (US)

(73) Assignee: ST. JUDE MEDICAL, LLC, Abbott Park, IL (US)

( * ) Notice: Subject to any disclaimer, the term of this patent is extended or adjusted under 35 U.S.C. 154(b) by 791 days.

(21) Appl. No.: 16/247,299

(22) Filed: Jan. 14, 2019

(65) Prior Publication Data

US 2019/0217057 A1 Jul. 18, 2019

Related U.S. Application Data

(63) Continuation of application No. 13/159,446, filed on Jun. 14, 2011, now Pat. No. 10,220,187.
(Continued)

(51) Int. Cl.
*A61B 18/14* (2006.01)
*A61M 25/00* (2006.01)
*A61B 18/00* (2006.01)

(52) U.S. Cl.
CPC ..... *A61B 18/1492* (2013.01); *A61M 25/0052* (2013.01); *A61B 2018/00404* (2013.01);
(Continued)

(58) Field of Classification Search
CPC ...... A61B 18/1492; A61B 2018/00404; A61B 2018/00434; A61B 2018/00511;
(Continued)

(56) References Cited

U.S. PATENT DOCUMENTS

| 4,325,374 A | 4/1982 | Komiya |
|---|---|---|
| 5,279,299 A | 1/1994 | Imran |

(Continued)

FOREIGN PATENT DOCUMENTS

| CN | 1897885 A | 1/2007 |
|---|---|---|
| JP | 03162588 B2 | 5/2001 |

(Continued)

OTHER PUBLICATIONS

H. Krum et al., "Catheter-based renal sympathetic denervation for resistance hypertension: a multicentre safety and proof-of-principle cohort study", www.thelancet.com, Mar. 30, 2009, pp. 1-7.
(Continued)

*Primary Examiner* — Michael F Peffley
*Assistant Examiner* — Samantha M Good
(74) *Attorney, Agent, or Firm* — Armstrong Teasdale LLP

(57) ABSTRACT

A catheter apparatus comprises an elongated catheter body having a distal end, a proximal end, and at least one fluid lumen extending longitudinally therein; and a plurality of flexible electrode segments on a distal portion of the catheter body adjacent the distal end, each pair of neighboring flexible electrode segments being spaced from each other longitudinally by a corresponding electrically nonconductive segment. Each flexible electrode segment comprises a sidewall provided with one or more elongated stiffness reductions extending through the sidewall, the one or more elongated stiffness reductions providing flexibility in the sidewall for bending movement relative to a longitudinal axis of the catheter body. The electrically nonconductive segment is substantially smaller in length than each of the corresponding pair of neighboring flexible electrode segments.

19 Claims, 11 Drawing Sheets

SECTION A-A

Related U.S. Application Data

(60) Provisional application No. 61/355,242, filed on Jun. 16, 2010.

(52) U.S. Cl.
CPC ............... *A61B 2018/00434* (2013.01); *A61B 2018/00511* (2013.01); *A61B 2018/00821* (2013.01); *A61B 2018/00869* (2013.01); *A61B 2018/00875* (2013.01); *A61B 2018/1407* (2013.01)

(58) Field of Classification Search
CPC ........... A61B 2018/00821; A61B 2018/00869; A61B 2018/00875; A61B 2018/1407; A61M 25/0052
See application file for complete search history.

(56) References Cited

U.S. PATENT DOCUMENTS

| | | |
|---|---|---|
| 5,364,352 A | 11/1994 | Cimino et al. |
| 5,378,230 A | 1/1995 | Mahurkar |
| 5,462,521 A | 10/1995 | Brucker et al. |
| 5,487,385 A | 1/1996 | Avitall |
| 5,520,682 A | 5/1996 | Baust et al. |
| 5,545,200 A | 8/1996 | West et al. |
| 5,569,220 A | 10/1996 | Webster, Jr. |
| 5,643,197 A | 7/1997 | Brucker et al. |
| 5,772,642 A | 6/1998 | Ciamacco, Jr. et al. |
| 5,800,428 A | 9/1998 | Nelson et al. |
| 5,810,802 A | 9/1998 | Panescu et al. |
| 5,833,632 A | 11/1998 | Jacobsen et al. |
| 5,853,425 A | 12/1998 | Houser |
| 5,893,885 A | 4/1999 | Webster, Jr. |
| 5,919,188 A | 7/1999 | Shearon et al. |
| 5,951,471 A | 9/1999 | de la Rama et al. |
| 5,954,719 A | 9/1999 | Chen et al. |
| 5,992,418 A | 11/1999 | de la Rama et al. |
| 6,001,095 A | 12/1999 | de la Rama et al. |
| 6,010,500 A | 1/2000 | Sherman et al. |
| 6,030,382 A | 2/2000 | Fleischman et al. |
| 6,063,080 A | 5/2000 | Nelson et al. |
| 6,210,409 B1 | 4/2001 | Ellman et al. |
| 6,217,573 B1 | 4/2001 | Webster |
| 6,233,476 B1 | 5/2001 | Strommer et al. |
| 6,235,022 B1 | 5/2001 | Hallock et al. |
| 6,251,134 B1 | 6/2001 | Alt et al. |
| 6,273,876 B1 | 8/2001 | Klima et al. |
| 6,308,090 B1 | 10/2001 | Tu et al. |
| 6,325,797 B1 | 12/2001 | Stewart et al. |
| 6,332,880 B1 | 12/2001 | Yang et al. |
| 6,346,104 B2 | 2/2002 | Daly et al. |
| 6,356,790 B1 | 3/2002 | Maguire et al. |
| 6,379,349 B1 | 4/2002 | Mueller et al. |
| 6,405,067 B1 | 6/2002 | Mest et al. |
| 6,463,632 B2 | 10/2002 | Craig, Jr. |
| 6,464,632 B1 | 10/2002 | Taylor |
| 6,493,590 B1 | 12/2002 | Wessman et al. |
| 6,498,944 B1 | 12/2002 | Ben Haim et al. |
| 6,522,930 B1 | 2/2003 | Schaer et al. |
| 6,604,003 B2 | 8/2003 | Fredricks et al. |
| 6,611,699 B2 | 8/2003 | Messing |
| 6,690,963 B2 | 2/2004 | Ben Haim et al. |
| 6,780,183 B2 | 8/2004 | Jimenez, Jr. et al. |
| 6,788,967 B2 | 9/2004 | Ben Haim et al. |
| 6,921,397 B2 | 7/2005 | Corcoran et al. |
| 6,980,843 B2 | 12/2005 | Eng et al. |
| 7,013,169 B2 | 3/2006 | Bowe |
| 7,137,395 B2 | 11/2006 | Fried et al. |
| 7,197,354 B2 | 3/2007 | Sobe |
| 7,263,397 B2 | 8/2007 | Hauck et al. |
| 7,386,339 B2 | 6/2008 | Strommer et al. |
| 7,386,399 B1 | 6/2008 | Izmailov et al. |
| 7,389,148 B1 | 6/2008 | Morgan |
| 7,416,552 B2 | 8/2008 | Paul et al. |
| 7,468,027 B2 | 12/2008 | Barbut et al. |
| 7,536,218 B2 | 5/2009 | Govari et al. |
| 7,537,595 B2 | 5/2009 | McClurken |
| 7,565,208 B2 | 7/2009 | Harris et al. |
| 7,669,309 B2 | 3/2010 | Johnson et al. |
| 7,699,771 B2 | 4/2010 | Wendlandt |
| 7,706,891 B2 | 4/2010 | Hastings et al. |
| 7,824,517 B2 | 11/2010 | Kampa et al. |
| 7,826,881 B1 | 11/2010 | Beatty et al. |
| 2001/0007070 A1 | 7/2001 | Stewart et al. |
| 2001/0012956 A1 | 8/2001 | Behl et al. |
| 2002/0058866 A1 | 5/2002 | Segner et al. |
| 2002/0072710 A1 | 6/2002 | Stewart et al. |
| 2003/0125730 A1 | 7/2003 | Berube et al. |
| 2004/0015215 A1 | 1/2004 | Fredricks et al. |
| 2004/0034348 A1 | 2/2004 | Rashidi |
| 2004/0064158 A1 | 4/2004 | Klein et al. |
| 2004/0143143 A1 | 7/2004 | Adger et al. |
| 2004/0143256 A1 | 7/2004 | Bednarek |
| 2004/0193239 A1 | 9/2004 | Falwell et al. |
| 2004/0204671 A1 | 10/2004 | Stubbs et al. |
| 2004/0220461 A1 | 11/2004 | Schwartz |
| 2004/0231683 A1 | 11/2004 | Eng et al. |
| 2004/0243143 A1 | 12/2004 | Corcoran et al. |
| 2004/0267106 A1 | 12/2004 | Segner et al. |
| 2005/0004563 A1 | 1/2005 | Racz et al. |
| 2005/0043713 A1 | 2/2005 | Zhou |
| 2005/0054989 A1 | 3/2005 | McGuckin et al. |
| 2005/0070894 A1 | 3/2005 | McClurken |
| 2005/0143729 A1 | 6/2005 | Francischelli et al. |
| 2005/0187561 A1 | 8/2005 | Lee et al. |
| 2005/0197633 A1 | 9/2005 | Schwartz et al. |
| 2005/0272975 A1 | 12/2005 | McWeeney et al. |
| 2006/0004353 A1 | 1/2006 | Koyfman et al. |
| 2006/0064123 A1 | 3/2006 | Bonnette et al. |
| 2006/0149192 A1 | 7/2006 | Deniega et al. |
| 2006/0200191 A1 | 9/2006 | Zadno Azizi |
| 2006/0287650 A1 | 12/2006 | Cao et al. |
| 2007/0005053 A1 | 1/2007 | Dando |
| 2007/0156114 A1 | 7/2007 | Worley et al. |
| 2007/0179491 A1 | 8/2007 | Kratoska et al. |
| 2007/0299424 A1 | 12/2007 | Cumming et al. |
| 2008/0091195 A1 | 4/2008 | Sliwa et al. |
| 2008/0125772 A1 | 5/2008 | Stone et al. |
| 2008/0139999 A1 | 6/2008 | Gibson et al. |
| 2008/0161788 A1 | 7/2008 | Dando et al. |
| 2008/0161789 A1 | 7/2008 | Thao et al. |
| 2008/0249522 A1 | 10/2008 | Pappone et al. |
| 2008/0275428 A1 | 11/2008 | Tegg et al. |
| 2008/0281319 A1 | 11/2008 | Paul et al. |
| 2008/0294158 A1 | 11/2008 | Pappone et al. |
| 2008/0300589 A1 | 12/2008 | Paul et al. |
| 2008/0312713 A1 | 12/2008 | Wilfley et al. |
| 2009/0012517 A1 | 1/2009 | de la Rama et al. |
| 2009/0228092 A1 | 9/2009 | Raeder-Devens et al. |
| 2009/0247993 A1 | 10/2009 | Kirschenman et al. |
| 2009/0287210 A1 | 11/2009 | Kauphusman et al. |
| 2010/0152731 A1 | 6/2010 | de la Rama et al. |
| 2010/0174177 A1 | 7/2010 | Wu |
| 2010/0286684 A1 | 11/2010 | Hata et al. |
| 2011/0118582 A1 | 5/2011 | De la Rama et al. |

FOREIGN PATENT DOCUMENTS

| | | |
|---|---|---|
| JP | 2006509547 A | 3/2006 |
| JP | 2002513652 A5 | 6/2006 |
| JP | 2008136875 A | 6/2008 |
| JP | 2008541799 A5 | 5/2009 |
| JP | 2010533564 A5 | 8/2011 |
| WO | 1995010327 A1 | 4/1995 |
| WO | 1996034652 A1 | 11/1996 |
| WO | 1997017904 A1 | 5/1997 |
| WO | 1999056812 A2 | 11/1999 |
| WO | 2002087453 A1 | 11/2002 |
| WO | 2005094661 A1 | 10/2005 |
| WO | 2007035554 A1 | 3/2007 |
| WO | 2008124619 A1 | 10/2008 |

(56) References Cited

FOREIGN PATENT DOCUMENTS

| WO | 2008147599 | A1 | 12/2008 |
| WO | 2009120982 | A2 | 10/2009 |
| WO | 2010129661 | A1 | 11/2010 |

OTHER PUBLICATIONS

PCT International Search Report (PCT/US2008/069248), dated Jan. 15, 2009, 2 pages.
"International Search Report and Written Opinion", PCT/US2011/040781 dated Nov. 25, 2011.
"International Search Report and Written Opinion", PCT/US2011/046266 dated Dec. 7, 2011.

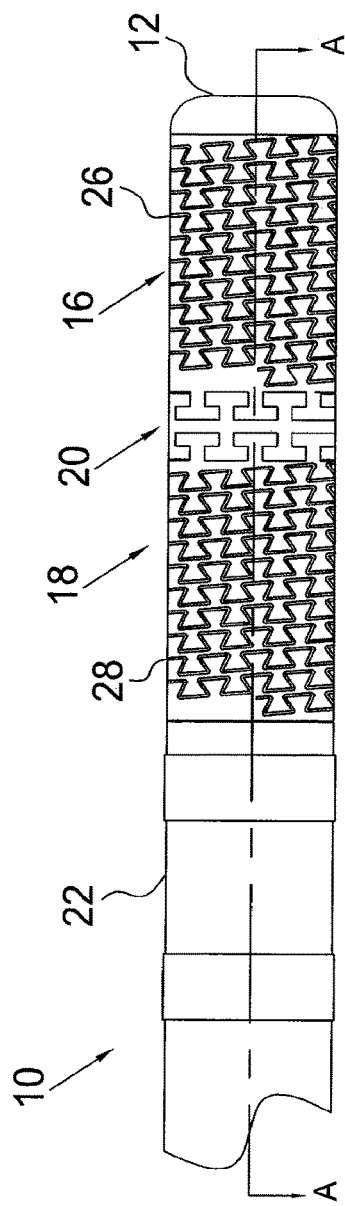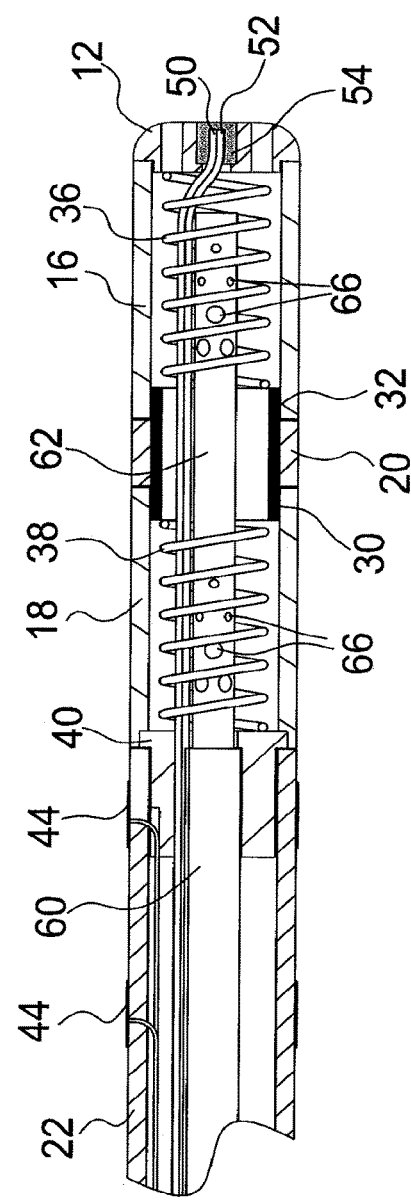

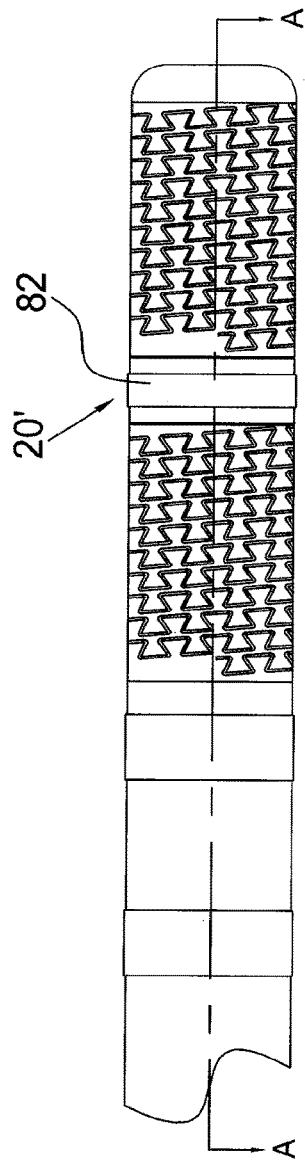
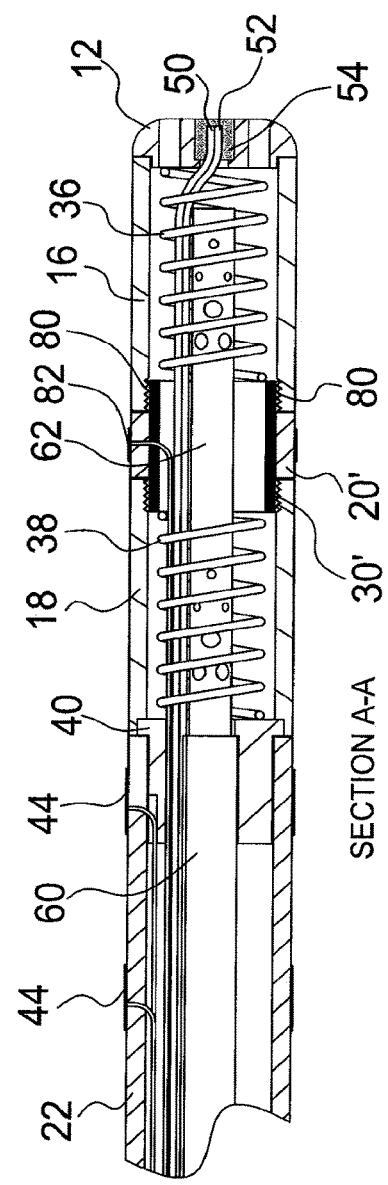

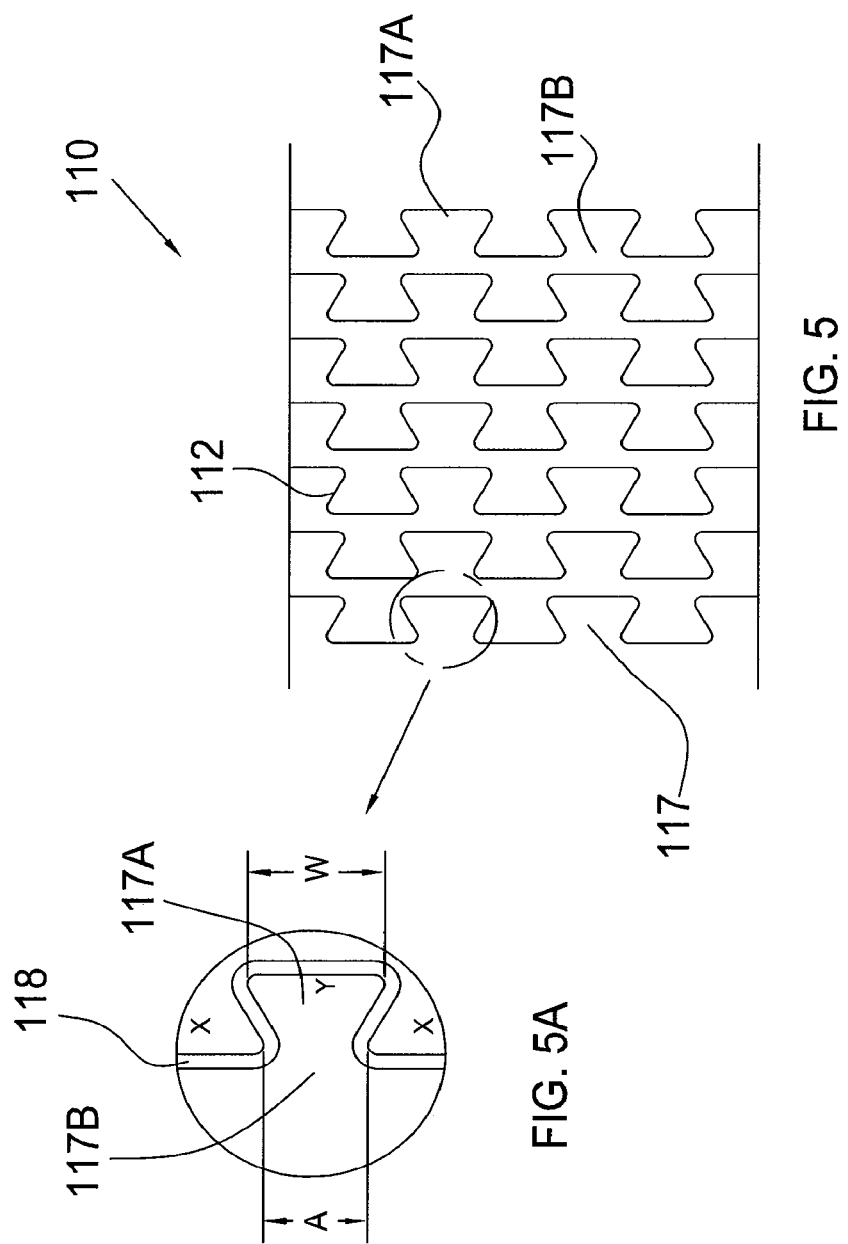

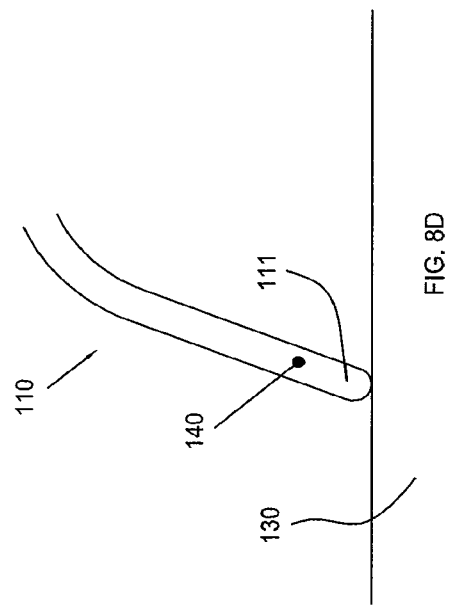
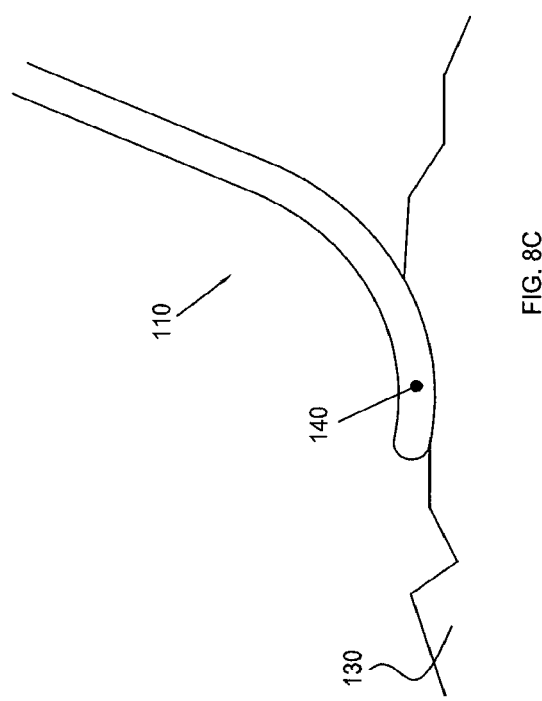

ABLATION CATHETER HAVING FLEXIBLE TIP WITH MULTIPLE FLEXIBLE ELECTRODE SEGMENTS

RELATED APPLICATIONS

This patent application is a Continuation of U.S. patent application Ser. No. 13/159,446 filed Jun. 14, 2011, now issued as U.S. Pat. No. 10,220,187, which claims the benefit of U.S. Provisional Application No. 61/355,242 filed Jun. 16, 2010, the entire disclosure of each of which is hereby incorporated by reference in its entirety.

BACKGROUND OF THE INVENTION

The present invention relates generally to catheter devices, and more specifically to an ablation catheter having a flexible tip with multiple flexible ablation electrode segments.

PCT Publication No. WO/2008/147599, entitled ABLATION CATHETER WITH FLEXIBLE TIP, published Dec. 4, 2008 (hereinafter "PCT 147599"), discloses flexible electrodes for catheters and catheter devices having such electrodes. The flexible electrode at the tip of the catheter provides, among other things, flexing and bending capability to the catheter tip to more effectively reach targeted tissues, even tissues having irregular surfaces with ridges and the like, and to more reliably create linear lesions on body tissue. The electrode is configured to provide a freedom of movement and shortening of a length of the catheter tip along its longitudinal axis to maintain surface contact with, for example, vibrating or moving tissue that is targeted for ablation. The entire content of the application is incorporated herein by reference.

BRIEF SUMMARY OF THE INVENTION

Exemplary embodiments of the invention provide a flexible tip for an ablation catheter, the flexible tip having two or more flexible electrode segments to produce multiple segmented ablation. Adjacent flexible ablation electrode segments are electrically isolated from one another by an electrically nonconductive segment. The length of the nonconductive segment is sufficiently small to allow the ablation zones of the two adjacent electrode segments to overlap in order to form a continuous lesion. This also preserves the overall flexibility of the distal portion of the ablation catheter by limiting the size of the nonconductive segment, which is non-flexible or at least not as flexible as the flexible electrode segments.

In accordance with an aspect of the present invention, a catheter apparatus comprises an elongated catheter body having a distal end, a proximal end, and at least one fluid lumen extending longitudinally therein; and a plurality of flexible electrode segments on a distal portion of the catheter body adjacent the distal end, each pair of neighboring flexible electrode segments being spaced from each other longitudinally by a corresponding electrically nonconductive segment. Each flexible electrode segment comprises a sidewall provided with one or more elongated stiffness reductions extending through the sidewall, the one or more elongated stiffness reductions providing flexibility in the sidewall for bending movement relative to a longitudinal axis of the catheter body. The electrically nonconductive segment is substantially smaller in length than each of the corresponding pair of neighboring flexible electrode segments.

In some embodiments, the electrically nonconductive segment is less than about 0.625 times of a length of each of the corresponding pair of neighboring flexible electrode segments. The electrically nonconductive segment is sufficiently small in length to provide substantially continuous flexibility across the flexible electrode segments and the corresponding electrically nonconductive segment. The catheter apparatus further comprises a plurality of spring coils corresponding to the plurality of flexible electrode segments, each of the spring coils being disposed within the catheter body and supported at both ends within the catheter body to provide resilient biasing support for the corresponding flexible electrode segment. Each of the spring coils biases the corresponding flexible electrode segment to stretch lengthwise. Each of the spring coils resiliently maintains the corresponding flexible electrode segment in a preset configuration in a resting state where no applied force is placed on the distal portion. The preset configuration for the corresponding flexible electrode segment is selected from the group consisting of a straight configuration and a curved configuration.

In specific embodiments, the one or more elongated stiffness reductions include a helical stiffness reduction forming a helical pattern on the sidewall and outlining alternating interlocking blocks. The one or more elongated stiffness reductions are selected from the group consisting of channels, gaps, grooves, and through-thickness openings. The one or more elongated stiffness reductions are one or more elongated through-thickness openings; and the at least one fluid lumen includes a lumen extension member, the lumen extension member extending along at least part of a length of each of the plurality of flexible electrode segments and having a plurality of openings configured and arranged to produce a predetermined fluid flow from the lumen extension member out of the one or more elongated through-thickness openings of each of the flexible electrode segments. The predetermined fluid flow is a substantially uniform fluid flow out of the one or more elongated through-thickness openings of each of the flexible electrode segments.

In some embodiments, the catheter apparatus further comprises a first diagnostic electrode disposed on the catheter body between at least one pair of neighboring flexible electrode segments. The catheter apparatus further comprises at least one second diagnostic electrode disposed on the catheter body proximally of the plurality of flexible electrode segments. A measurement circuit is coupled with the plurality of flexible electrode segments to perform impedance measurement of measuring impedance associated with tissue-electrode coupling. A processor is coupled with the measurement circuit and configured to determine at least one of reactance component or phase angle component of the impedance measurement, and based on the at least one of reactance component or phase angle component, to determine a corresponding tissue-electrode coupling condition for each of the plurality of flexible electrode segments. A memory stores previously determined results of tissue-electrode coupling conditions corresponding to various at least one of reactance components or phase angle components for a range of tissue types and at various frequencies of electrical energy supplied to the plurality of flexible electrode segments for the impedance measurement, wherein the results are to be used by the processor to determine the corresponding tissue-electrode coupling condition.

In accordance with another aspect of the invention, a catheter apparatus comprises an elongated catheter body having a distal end, a proximal end, and at least one fluid lumen extending longitudinally therein; and a plurality of flexible electrode segments on a distal portion of the catheter body adjacent the distal end, each pair of neighboring flexible electrode segments being spaced from each other longitudinally by a corresponding electrically nonconductive segment. Each flexible electrode segment comprises a sidewall provided with one or more elongated stiffness reductions extending through the sidewall, the one or more elongated stiffness reductions providing flexibility in the sidewall for bending movement relative to a longitudinal axis of the catheter body. The electrically nonconductive segment is less than about 0.625 times of a length of each of the corresponding pair of neighboring flexible electrode segments.

In some embodiments, the electrically nonconductive segment is less than about 1.09 times of a diameter of the distal portion.

In accordance with another aspect of this invention, a catheter apparatus comprises an elongated catheter body having a distal end, a proximal end, and at least one fluid lumen extending longitudinally therein; and a plurality of flexible electrode segments on a distal portion of the catheter body adjacent the distal end, each pair of neighboring flexible electrode segments being spaced from each other longitudinally by a corresponding electrically nonconductive segment. Each flexible electrode segment comprises a sidewall provided with one or more elongated stiffness reductions extending through the sidewall, the one or more elongated stiffness reductions providing flexibility in the sidewall for bending movement relative to a longitudinal axis of the catheter body. The electrically nonconductive segment is smaller in length than each of the corresponding pair of neighboring flexible electrode segments. The electrically nonconductive segment is less than about 1.09 times of a diameter of the distal portion.

In some embodiments, a ratio between a length of each of the corresponding pair of neighboring flexible electrode segments and a diameter of the distal portion is less than about 1.7.

These and other features and advantages of the present invention will become apparent to those of ordinary skill in the art in view of the following detailed description of the specific embodiments.

BRIEF DESCRIPTION OF THE DRAWINGS

FIG. 1 is an elevational view of a distal portion of an ablation catheter according to a first embodiment of the present invention.

FIG. 2 is a partial cross-sectional view of the distal portion of the ablation catheter of FIG. 1.

FIG. 3 is an elevational view of a distal portion of an ablation catheter according to a second embodiment of the present invention.

FIG. 4 is a partial cross-sectional view of the distal portion of the ablation catheter of FIG. 3.

FIG. 5 is an elevational view illustrating an interlocking pattern for the flexible electrode segment of a multi-segmented flexible tip.

FIG. 5A is a magnified view of a portion of FIG. 5.

FIG. 8C is an elevational view of the multi-segmented flexible tip shown in FIG. 8B being dragged across tissue having ridges thereon.

FIG. 8D is an elevational view of the multi-segmented flexible tip being dragged across a smooth tissue surface.

DETAILED DESCRIPTION OF THE INVENTION

Figure 7:
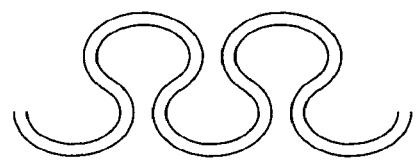
FIG. 7 is an elevational view of an alternative section of the flexible electrode segment of FIG. 5.

FIG. 1 is an elevational view of a distal portion 10 of an ablation catheter according to an embodiment of the present invention. The distal portion 10 includes a distal end 12 which is flat with a rounded corner but may have other shapes such as the shape of a dome in alternative embodiments. The distal portion 10 further includes two flexible electrode segments 16, 18 which are separated by an electrically nonconductive segment 20. In alternative embodiments, there may be multiple nonconductive segments each separating two neighboring flexible electrode segments. The distal flexible electrode segment 16 is coupled with the distal end 12 and the proximal flexible electrode segment 18 is coupled with a catheter shaft 22. The flexible electrode segments 16, 18 each have a cylindrical sidewall with a series of annular or ring-like surface channels, gaps, grooves, or through-thickness openings 26, 28, respectively, cut or otherwise formed into the sidewall. Elongated gaps define elongated areas of decreased wall thickness and decreased cross-sectional area of the sidewall, while elongated openings extend completely through the thickness of the sidewall. These elongated features including gaps and openings are referred to herein as elongated stiffness reductions. As used herein, an elongated gap or opening preferably has a length that is at least about 3 times the width of the gap or opening, more preferably at least about 5 times, and most preferably at least about 10 times.

Various configurations and details of the elongated gaps and openings are provided in PCT 147599. In one example, multiple elongated stiffness reductions are annular and extend generally parallel to one another. Each annular stiffness reduction extends in a plane that is generally perpendicular to a longitudinal axis of the tip electrode. The respective stiffness reductions may be spaced equidistant from each other along a longitudinal length of the tip electrode. Each annular stiffness reduction may form a continuous 360 degree unending loop that is circular. Alternatively, all or part of the series of stiffness reductions may extend in a non-circular and a non-planar helical configuration completing more than one 360 degree loop or turn on the surface of the electrode sidewall, with the helical stiffness reductions having discrete end points. In FIG. 1, the elongated openings 26, 28 each form an interlocking pattern that follows a continuous spiral path configuration from one end of the flexible electrode segment to the other end.

FIG. 5 is an elevational view illustrating an interlocking pattern for the flexible electrode segment. FIG. 5A is a magnified view of a portion of FIG. 5. The flexible electrode segment in the multi-segmented flexible tip 110 has an elongated cutting pattern in the electrode sidewall that outlines alternating interlocking blocks 117. In the illustrated embodiment, the contemplated blocks 117 are disposed on both sides of an elongated gap 118 created by the cutting pattern. Each block has a head 117A and a neck 117B, and the head 117A is wider than the neck 117B in each block. A first head, represented by "Y" in FIG. 5A of the block 117, which has a neck 117B situated on one side of the gap 118, is disposed between a second and third heads represented by "X" in FIG. 5A. The second and third heads X each have necks situated on the other side of the elongated gap 118 and opposing the head Y. The blocks X and Y are interlocked because the wider head portion of one block 117 is locked between the narrower neck portions of the two adjacent blocks 117. For example, the second and third heads X in FIG. 5A are separated by a shortest distance A in FIG. 9A, and distance A is shorter than a width W of the head Y, thereby restricting relative movement of two adjacent loops away from each other and preventing the blocks from separating.

Figure 6:
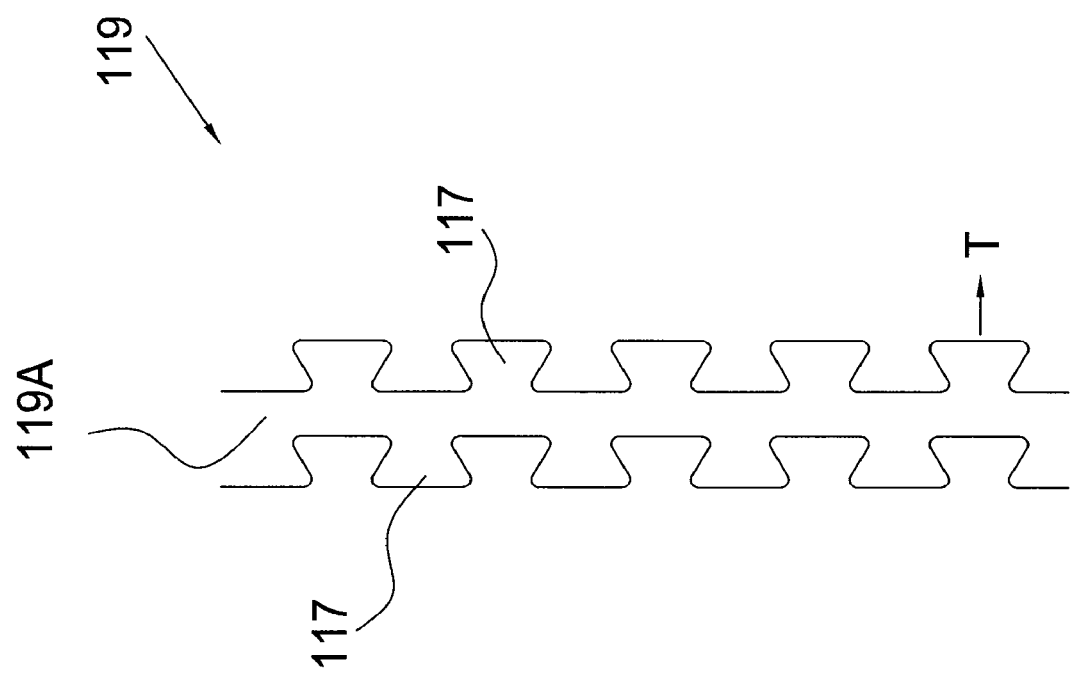
FIG. 6 is an elevational view of a section of the flexible electrode segment of FIG. 5.

Contemplated patterns of elongated openings can also be described by focusing on the structures of the electrode wall, instead of focusing on the shape of the gap 118. For example, FIG. 6 is an elevational view of a section of the flexible electrode segment of FIG. 5. A contemplated electrode wall includes a stem member 119 that may either form discrete annular loops or helically extend about a longitudinal axis of the electrode forming a series of stem loops (see FIG. 5), wherein the stem member 119 includes a plurality of protruding blocks 117 peripherally disposed on both sides of the stem member 119. Each block 117 transversely extends in a lateral direction indicated by arrow T in FIG. 6 toward an adjacent stem loop in the electrode wall shown in FIG. 5. Each adjacent stem loop includes blocks 117 that are staggered from the blocks 117 in immediately adjacent stem loops, resulting in an interlocking block pattern. Contemplated blocks for the stem member can have various shapes. For example, at least some of the blocks 117 may have a shape of an upside down triangle as illustrated, where one angle of the triangle represents the neck region. Alternatively, blocks with rounded bulbous shape such as ones shown in FIG. 7 may alternatively be utilized. Contemplated heads of the bulbous shapes are wider than their corresponding necks, facilitating an interlocking block pattern.

Figure 8B:
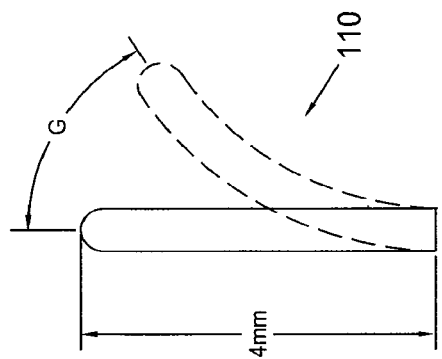
FIG. 8B is an elevational view of a multi-segmented flexible tip showing a degree of flexing.
Figure 8A:
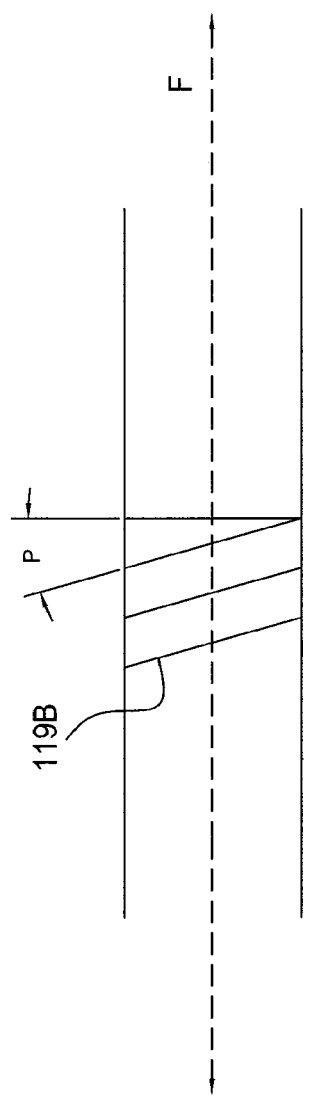
FIG. 8A is schematic illustration of a helical pattern for flexible electrode segment of FIG. 5.

The stem members of FIGS. 6 and 7, for example, having an axis 119A, may extend in a helix about the longitudinal axis F in FIG. 8A with a pitch P between and including 0.5 to 10 degrees. To describe it in another way, the patterns of elongated gaps 118 extend helically around the longitudinal axis F with a pitch angle, for example, between and including 0.5 to 10 degrees.

The contemplated elongated openings defining the gaps 118 between the blocks of the stem members (FIG. 5) improve a flexibility of the electrode, and allow the electrode to flex and bend along the longitudinal length of the electrode and relative to the catheter body to which it is attached. For example, the ability of the flexible electrode segment to flex allows an approximately 4 mm length of the electrode segment to bend at an angle G in FIG. 8B that falls, for example, between and including about 0.2 degrees to 70 degrees relative to the longitudinal axis from a substantially straight position. More specifically, the ability to flex allows the approximately 4 mm electrode segment length to bend between and including about 5 degrees to 50 degrees relative to the longitudinal axis from a substantially straight position. Even more specifically, the ability to flex allows the approximately 4 mm segment length to bend about 22 degrees relative to the longitudinal axis from a substantially straight position.

FIGS. 8C and 8D illustrate a multi-segmented flexible tip 110 being dragged across tissue 130. In FIG. 8C, the multi-segmented flexible tip 110 is flexed and pressed against tissue 130, which has a relatively irregular surface. Being able to flex provides better contact with the target tissue, for example, in the trabeculated endocardial tissue where there are valleys, ridges, and pockets in the tissue surface. Here, electrode-to-tissue contact area is increased by using the side of the multi-segmented flexible tip 110 to deliver energy for ablation. The increased contact surface increases the likelihood of creating larger lesions at a given contact force and power setting. This in turn enables deeper ablation without having to increase the power setting, which is beneficial because increased power settings undesirably increase the likelihood of coagulation. In FIG. 8D, the dome tip 111 is used to delivery energy to tissue 130.

The multi-segmented flexible tip 110 also capably absorbs any contraction or vibration of tissue 130, and improves continuous tissue contact in a beating heart during systole and diastole, whether the electrode contacts the tissue 130 in a parallel, perpendicular, or other orientation. Continuous tissue contact is also assured regardless of whether the electrode is stationary at one location or when the electrode is in motion being dragged. Without such flexibility, a standard rigid tip electrode would "jump off" of the tissue in response to a beating heart.

The electrically nonconductive segment 20 electrically isolates the two flexible electrode segments 16, 18. It also serves to connect and secure the two flexible electrode segments. As seen in FIG. 1, the nonconductive segment 20 has T-shaped protrusions that match the corresponding T-shaped voids or cavities on the edges of the two flexible electrode segments 16, 18 to form interlocking connections to secure the coupling between the electrode segments 16, 18. Of course, other configurations can be used to form the connections. The nonconductive segment 20 is made of polyimide or some other nonconductive material. It may be formed as a strip and then bent into a tubular shape to form the interconnecting coupling between the two electrode segments 16, 18.

The length of the nonconductive segment 20 is sufficiently small to allow the ablation zones of the two adjacent electrode segments to overlap in order to form a continuous lesion. For each ablation element, the ablation zone is a region that is energized with sufficient energy to ablate tissue or denervate nerves within the ablation zone. For RF ablation or the like, the ablation zones are typically similar in shape as but larger in size than the corresponding ablation elements 16, 18. In the longitudinal direction, the ablation zones for the ablation elements 16, 18 will be longer than the ablation elements to reach across the gap caused by the nonconductive segment 20 so as to produce a continuous lesion. The short nonconductive segment 20 also preserves the overall flexibility of the distal portion 10 of the ablation catheter by limiting the size of the nonconductive segment 20, which is non-flexible or at least not as flexible as the flexible electrode segments 16, 18. The distal portion 10 preferably has substantially continuous flexibility across the flexible electrode segments and the nonconductive segment(s). For instance, the flexural modulus of the distal portion 10 is increased by no more than 20% by including the nonconductive segment(s) 20, preferably no more than 10%, and more preferably no more than 5%. Therefore, it is critical that the length of the nonconductive segment 20 be substantially smaller than the length of the flexible electrode segments 16, 18 (i.e., at least about 30% smaller in length).

In one example of a 7 French catheter (2.3 mm diameters), the flexible electrode segments 16, 18 are each about 4 mm in length while the nonconductive segment 20 is about 1 mm in length. The nonconductive segment 20 is substantially smaller in length than the flexible electrode segments 16, 18. The length ratio is preferably less than about 0.625 (2.5 mm divided by 4 mm), more preferably less than about 0.5 (2 mm divided by 4 mm), and most preferably less than about 0.25 (1 mm divided by 4 mm). The length to diameter ratio between the length of the nonconductive segment 20 and the diameter of the catheter at the distal portion 10 is typically less than about 1.09 (2.5 mm divided by 2.3 mm), preferably less than about 0.87 (2 mm divided by 2.3 mm), and more preferably less than about 0.43 (1 mm divided by 2.3 mm). The ratio between the length of each flexible electrode segment 16, 18 and the diameter of the catheter at the distal portion 10 is typically less than about 1.7 (4 mm divided by 2.3 mm).

FIG. 2 is a partial cross-sectional view of the distal portion 10 of the ablation catheter of FIG. 1. A tube 30 is disposed internally between the flexible electrode segments 16, 18, and is attached to the flexible electrode segments 16, 18 by an adhesive 32 or the like. The tube 30 may be a PEEK tube or it may be made of other suitable nonconductive materials. A distal spring coil 36 is supported between the distal end 12 and the tube 30. A proximal spring coil 38 is supported between the tube 30 and a tip stem 40 which is disposed between and attached to the proximal electrode segment 18 and the catheter shaft 22. The spring coils 36, 38 provide resilient biasing supports for the flexible electrode segments 16, 18, respectively, particularly when the segments have through-thickness openings instead of grooves. The spring coils 36, 38 provide structural integrity to the electrode walls and resiliently maintain the flexible electrode segments 16, 18 in a predetermined configuration in a resting state where no applied force is placed on the electrode. In the embodiment shown, the predetermined electrode configuration at rest orients the longitudinal axis of each electrode segment to follow a straight line. In a different embodiment, the predetermined configuration at rest may orient the longitudinal axes of the electrode segments along a curved or arcuate path (see, e.g., PCT 147599).

Figure 10:
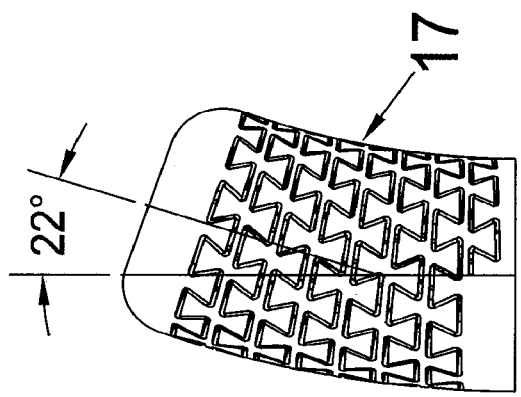
FIG. 10 is an elevational view schematically illustrating bending of one flexible electrode segment.
Figure 9:
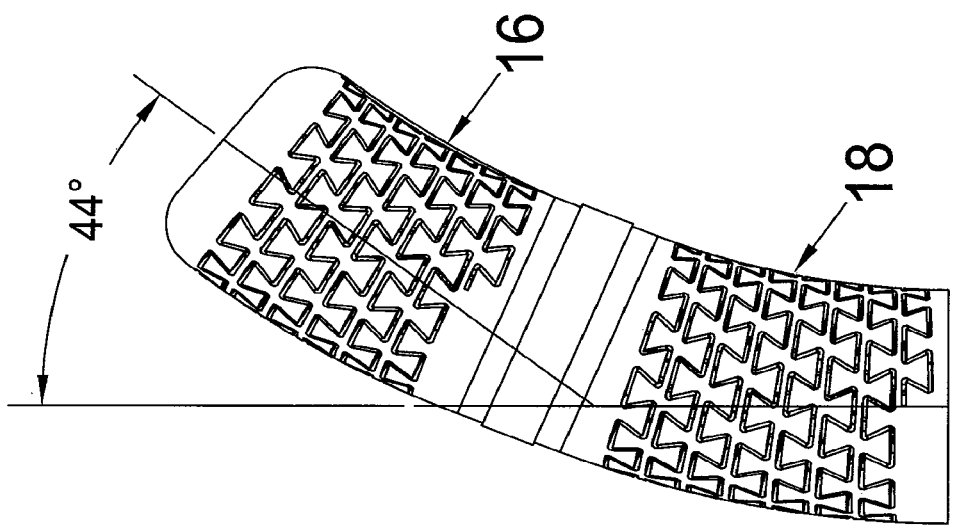
FIG. 9 is an elevational view schematically illustrating bending of the distal portion of the ablation catheter having two flexible electrode segments.

FIG. 9 is an elevational view schematically illustrating bending of the distal portion of the ablation catheter having two flexible electrode segments 16, 18. FIG. 10 is an elevational view schematically illustrating bending of one flexible electrode segment 17. In FIGS. 9 and 10, each flexible electrode segment makes a 22° turn under the applied force. FIG. 9 shows a total 44° turn for the two flexible electrode segments. The use of multiple flexible electrode segments (FIG. 9) produces a higher degree turn for the distal portion as well as a longer ablation zone as compared to a single flexible electrode (FIG. 10).

The contemplated coils 36, 38 resiliently bias the electrode segments 16, 18 to axially stretch in the direction that is generally parallel to the longitudinal axes of the electrode segments 16, 18. In other words, the coils optionally bias the flexible electrode segments to stretch lengthwise. When deflected from the predetermined configuration under applied force, the electrode segments may resiliently return to the predetermined configuration when the applied force is released. The electrode segments 16, 18 are made of suitable conductive and biocompatible materials, suitable for ablation temperature; such materials include natural and synthetic polymers, various metals and metal alloys, Nitinol, MP35N alloy, platinum-iridium (Pt—Ir) alloy (e.g., 90-10 or 80-20 alloy), naturally occurring materials, textile fibers, and combinations thereof. The coils 36, 38, or the electrode segments 16, 18, or both coils and electrode segments, may be fabricated from a shape memory material such as Nitinol.

As seen in FIGS. 1 and 2, a pair of band electrodes 44 are provided on the catheter shaft 22 (proximal of the flexible electrode segments 16, 18) and may be used for diagnostic purposes or the like. Conductor wires 50 and thermocouples 52 are provided. FIG. 2 shows urethane adhesive 54 at the distal end 12 for the conductor wire(s) 50 and thermocouple(s) 52; the conductor wires 50 and thermocouples 52 may also be provided at other locations at or near other electrodes or electrode segments.

FIG. 2 shows a lumen tubing 60 leading distally to an extension lumen tubing 62 which extends along much of the lengths of the two flexible electrode segments 16, 18. The lumen extension tubing 62 is coupled to the lumen tubing 60 via a suitable coupling mechanism such as heat fusion, adhesion, and/or laser welding. Alternatively, the lumen extension tubing 62 is formed integrally with the lumen tubing 60. The extension lumen tubing 62 defines an extended fluid lumen extending therethrough, and enables channeling fluid from the lumen tubing 60 along a longitudinal length of the distal portion 10. As such, the extended fluid lumen of the tubing 62 is in fluid communication with the fluid lumen of the lumen tubing 60, and the extension lumen tubing 62 has openings 66 of sizes and arrangements to provide a desired (e.g., substantially uniform) irrigation pattern or fluid flow within the distal portion 10 flowing out of the elongated openings 26, 28 of the flexible electrode segments 16, 18. The lumen extension tubing 62 extends to the openings 66 configured to produce a dedicated distribution of fluid to the openings 66. Channeling a dedicated distribution of fluid through the lumen extension tubing 62 facilitates controlling fluid channeled through the openings 66 to produce a desired irrigation pattern (e.g., substantially uniform). Additional details of the extension lumen tubing can be found in U.S. Patent Application Publication No. 2010/0152731, which is incorporated herein by reference in its entirety.

FIG. 3 is an elevational view of a distal portion of an ablation catheter according to a second embodiment of the present invention. FIG. 4 is a partial cross-sectional view of the distal portion of the ablation catheter of FIG. 3. The second embodiment differs from the first embodiment in the configurations of the electrically nonconductive segment 20' and tube 30' and the connection they provide to the flexible electrode segments in the second embodiment instead of the electrically nonconductive segment 20 and the tube 30 in the first embodiment. In the second embodiment, the tube 30' has external threads to engage inner threads of the electrically nonconductive segment 20' and the two flexible electrode segments 16, 18, so as to provide threaded connection 80. Another band electrode 82 may be provided on the nonconductive segment 20' for diagnostic purposes or the like. For instance, the diagnostic electrodes 44, 82 can be used to alleviate far field potential. For a nonconductive segment 20' that is about 1 mm in length in the longitudinal direction, the band electrode 82 is typically about 0.25 to about 0.5 mm in length. The one or more proximal electrodes 44 each may have about the same length as, or a larger length than, the band electrode 82. In one example, the electrode 82 has a length of about 0.5 mm and the one or more proximal electrodes 44 each have a length of about 1 mm.

FIGS. 1-4 show two flexible electrode segments. In other embodiments, there may be three or more flexible electrode segments. Each pair of neighboring flexible electrode segments are separated by an electrically nonconductive segment.

Recent angiographic studies have shown a highly variable cavotricuspid isthmus anatomy with various configurations and topography, which may lead to difficulties in some atrial flutter cases. Placing a long-tipped, rigid 8 mm electrode into pouch-like recesses found in these patients may present technical challenges. The multi-segmented flexible tip catheter design may better enable to synchronously maintain tissue contact with the beating heart and also facilitate the creation of a linear lesion. This flexible tip may also be advantageous in ablating within the trabeculated endocardial regions of patients with ventricular tachyarrhythmias, and in ablating the roof lines in atrial fibrillation procedures. It may also be useful when ablating within the coronary sinus.

Another application is for ablating renal sympathetic nerves in therapeutic renal sympathetic denervation to achieve reductions of blood pressure in patients suffering from renal sympathetic hyperactivity associated with hypertension and its progression. Renal sympathetic efferent and afferent nerves, which lie within and immediately adjacent to the wall of the renal artery, are crucial for initiation and maintenance of systemic hypertension. Indeed, sympathetic nerve modulation as a therapeutic strategy in hypertension had been considered long before the advent of modern pharmacological therapies. Renal denervation is the application of a chemical agent, or a surgical procedure, or the application of energy to remove/damage renal nerves to diminish completely the renal nerve functions. This is a complete and permanent block of the renal nerves. Renal denervation diminishes or reduces renal sympathetic nerve activity, increases renal blood flow (RBF), and decreases renal plasma norepinephrine (NE) content. The catheter will be sized differently for ablating or denervating nerves located within and around different vessels and walls. For example, the size of the catheter for ablating renal sympathetic nerves is typically smaller than that for ablating around a pulmonary vein (e.g., up to about 5 French instead of about 7 French).

During an exemplary ablation procedure, a user (e.g., the patient's physician or a technician) may insert the electrode catheter into one of the patient's blood vessels. The user, guided by a real-time fluoroscopy imaging device (not shown), moves the electrode catheter into the patient's heart. When the electrode catheter reaches the patient's heart, the electrodes at the tip of the electrode catheter may be implemented to electrically map the myocardium and locate a target tissue. After locating the target tissue, the user must move the electrode catheter into contact and electrically couple the catheter electrode with the target tissue before applying ablative energy to form an ablative lesion or lesions. The electrode-tissue contact refers to the condition when the catheter electrode physically touches the target tissue thereby causing a mechanical coupling between the catheter electrode and the target tissue. Electrical coupling refers to the condition when a sufficient portion of electrical energy passes from the catheter electrode to the target tissue so as to allow efficient lesion creation during ablation. For target tissues with similar electrical and mechanical properties, electrical coupling includes mechanical contact. That is, mechanical contact is a subset of electrical coupling. Thus, the catheter electrode may be substantially electrically coupled with the target tissue without being in mechanical contact, but not vice-versa. In other words, if the catheter electrode is in mechanical contact, it is also electrically coupled. The range or sensitivity of electrical coupling, however, changes for tissues with different electrical properties. For example, the range of electrical coupling for electrically conductive myocardial tissue is different from the vessel walls. Likewise, the range or sensitivity of electrical coupling also changes for tissues with different mechanical properties, such as tissue compliance. For example, the range of electrical coupling for the relatively more compliant smooth atrial wall is different from the relatively less compliant pectinated myocardial tissue. The level of contact and electrical coupling are often critical to form sufficiently deep ablative lesions on the target tissue without damaging surrounding tissue in the heart. The catheter system may be implemented to measure impedance at the electrode-tissue interface and assess the level of contact between the electrode catheter and the target tissue.

Exemplary levels of contact or coupling may include "little or no contact," "light to medium contact," and "hard contact." Contact condition of "little or no contact" may be experienced before the electrode catheter comes into contact with the target tissue. Insufficient contact may inhibit or even prevent adequate lesions from being formed when the electrode catheter is operated to apply ablative energy. However, contact condition of "hard contact" may result in the formation of lesions which are too deep (e.g., causing perforations in the myocardium) and/or the destruction of tissue surrounding the target tissue. Accordingly, the user may desire contact condition of "light to medium contact."

Figure 11:
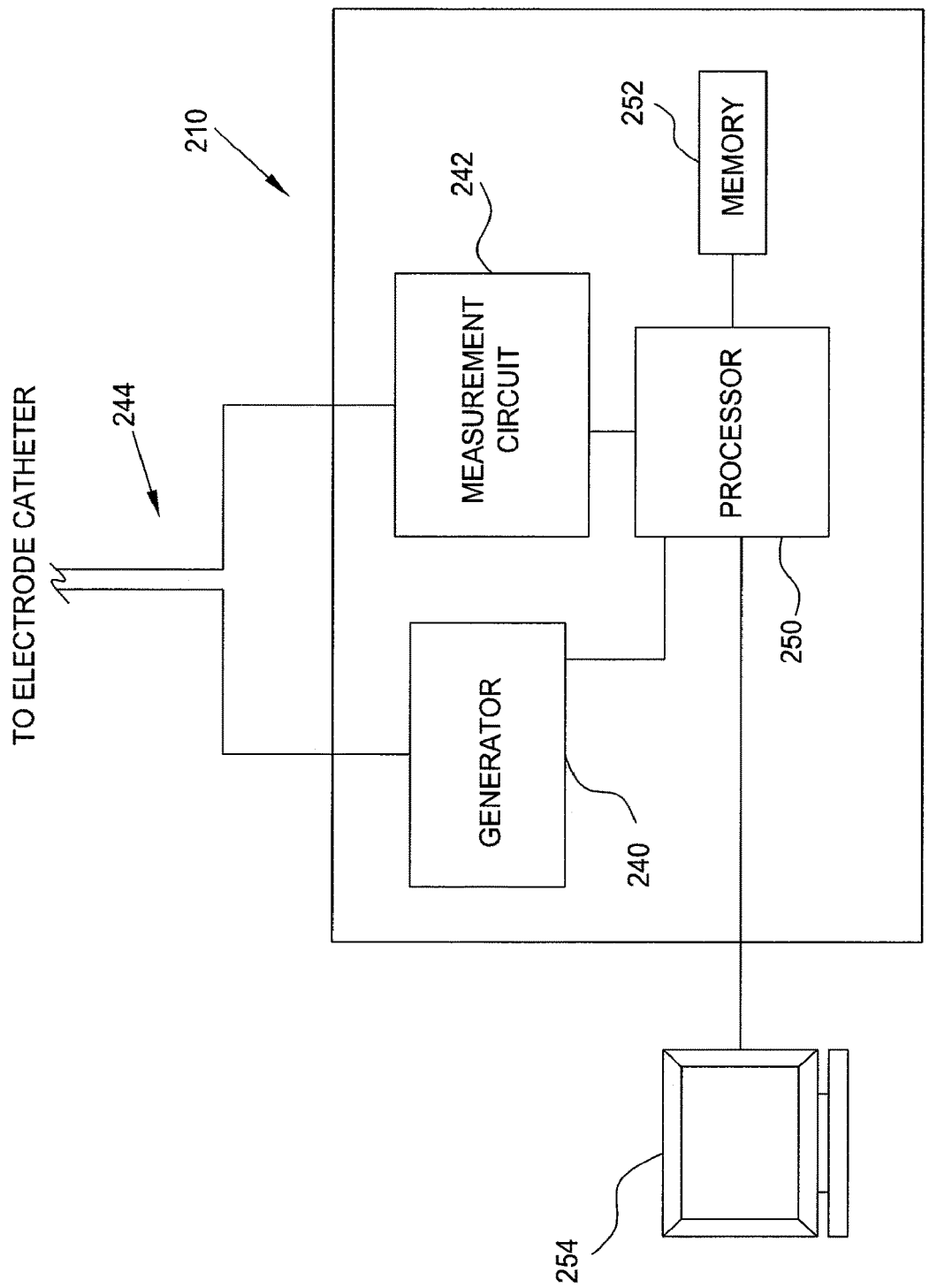
FIG. 11 is a high-level functional block diagram showing a catheter system as it may be implemented to assess contact or coupling conditions for an electrode catheter.

FIG. 11 is a high-level functional block diagram showing the catheter system 210 in more detail as it may be implemented to assess contact or coupling conditions for the electrode catheter. It is noted that some of the components typical of conventional tissue ablation systems are shown in simplified form and/or not shown at all for purposes of brevity. Such components may nevertheless also be provided as part of, or for use with, the catheter system 210. For example, the electrode catheter may include a handle portion, a fluoroscopy imaging device, and/or various other controls, to name only a few examples. Such components are well understood in the medical devices arts and therefore further discussion herein is not necessary for a complete understanding of the invention.

The exemplary catheter system 210 may include a generator 240, such as, e.g., a radio frequency (RF) generator, and a measurement circuit 242 electrically connected to the electrode catheter (as illustrated by wires 244 to the electrode catheter). The electrode catheter may also be electrically grounded, e.g., through grounding patch affixed to the patient's arm or chest. The generator 240 may be operated to emit electrical energy (e.g., RF current) near the tip of the electrode catheter. It is noted, that although the embodiment is described herein with reference to RF current, other types of electrical energy may also be used for assessing contact conditions.

In an exemplary embodiment, the generator 240 emits a so-called "pinging" (e.g., low) frequency as the electrode catheter approaches the target tissue. The "pinging" frequency may be emitted by the same electrode catheter that is used to apply ablative energy for lesion formation. Alternatively, a separate electrode catheter may be used for applying the "pinging" frequency. In such an embodiment, the separate electrode may be in close contact with (or affixed to) the electrode for applying ablative energy so that a contact or coupling condition can be determined for the electrode which will be applying the ablative energy.

The resulting impedance at the electrode-tissue interface may be measured during contact or coupling assessment (or "pinging") using a measurement circuit 242. In an exemplary embodiment, the measurement circuit 242 may be a conventionally available resistance-capacitance-inductance (RCL) meter. Another exemplary measurement circuit which may be implemented for determining the phase angle component is also described in more detail below with reference to FIG. 12. Still other measurement circuits 242 may be implemented and the invention is not limited to use with any particular type or configuration of measurement circuit. The reactance and/or phase angle component of the impedance measurements may be used to determine a contact or coupling condition. The contact or coupling condition may then be conveyed to the user in real-time for achieving the desired level of contact or coupling for the ablation procedure. For example, the contact or coupling condition may be displayed for the user on a light array.

After the user has successfully guided the electrode catheter into the desired contact or coupling condition with the target tissue, a generator, such as generator 240 or a second generator, may be operated to generate ablative (e.g., high frequency) energy for forming an ablative lesion or lesions on the target tissue. In an exemplary embodiment, the same generator 240 may be used to generate electrical energy at various frequencies both for the impedance measurements (e.g., "pinging" frequencies) and for forming the ablative lesion. In alternative embodiments, however, separate generators or generating units may also be implemented without departing from the scope of the invention.

In an exemplary embodiment, the measurement circuit 242 may be operatively associated with a processor 250 and a memory 252 to analyze the measured impedance. By way of example, the processor 250 may determine a reactance and/or phase angle component of the impedance measurement, and based on the reactance component and/or phase angle, the processor 250 may determine a corresponding contact or coupling condition for the electrode catheter. In an exemplary embodiment, contact or coupling conditions corresponding to various reactance and/or phase angles may be predetermined, e.g., during testing for any of a wide range of tissue types and at various frequencies. The contact or coupling conditions may be stored in the memory 252, e.g., as tables or other suitable data structures. The processor 250 may then access the tables in the memory 252 and determine a contact or coupling condition corresponding to impedance measurement based on the reactance component and/or phase angle. The contact or coupling condition may be output for the user, e.g., at the display device 254.

It is noted that the catheter system 210 is not limited to use with the processor 250 and memory 252. In other embodiments, analog circuitry may be implemented for assessing contact conditions based on the impedance measurement and for outputting a corresponding contact condition. Such circuitry may be readily provided by one having ordinary skill in the electronics arts after having become familiar with the teachings herein, and therefore further discussion is not needed. It is also noted that display device 254 is not limited to any particular type of device. For example, display device 254 may be a computer monitor such as a liquid-crystal display (LCD). Alternatively, the display device may be implemented as a light array, wherein one or more light emitting diodes (LED) are activated in the light array to indicate a contact condition (e.g., more lights indicating more contact). Indeed, any suitable output device may be implemented for indicating contact conditions to a user, and is not limited to a display device. For example, the contact condition may be output to the user as an audio signal or tactile feedback (e.g., vibrations) on the handle of the electrode catheter.

Figure 12:
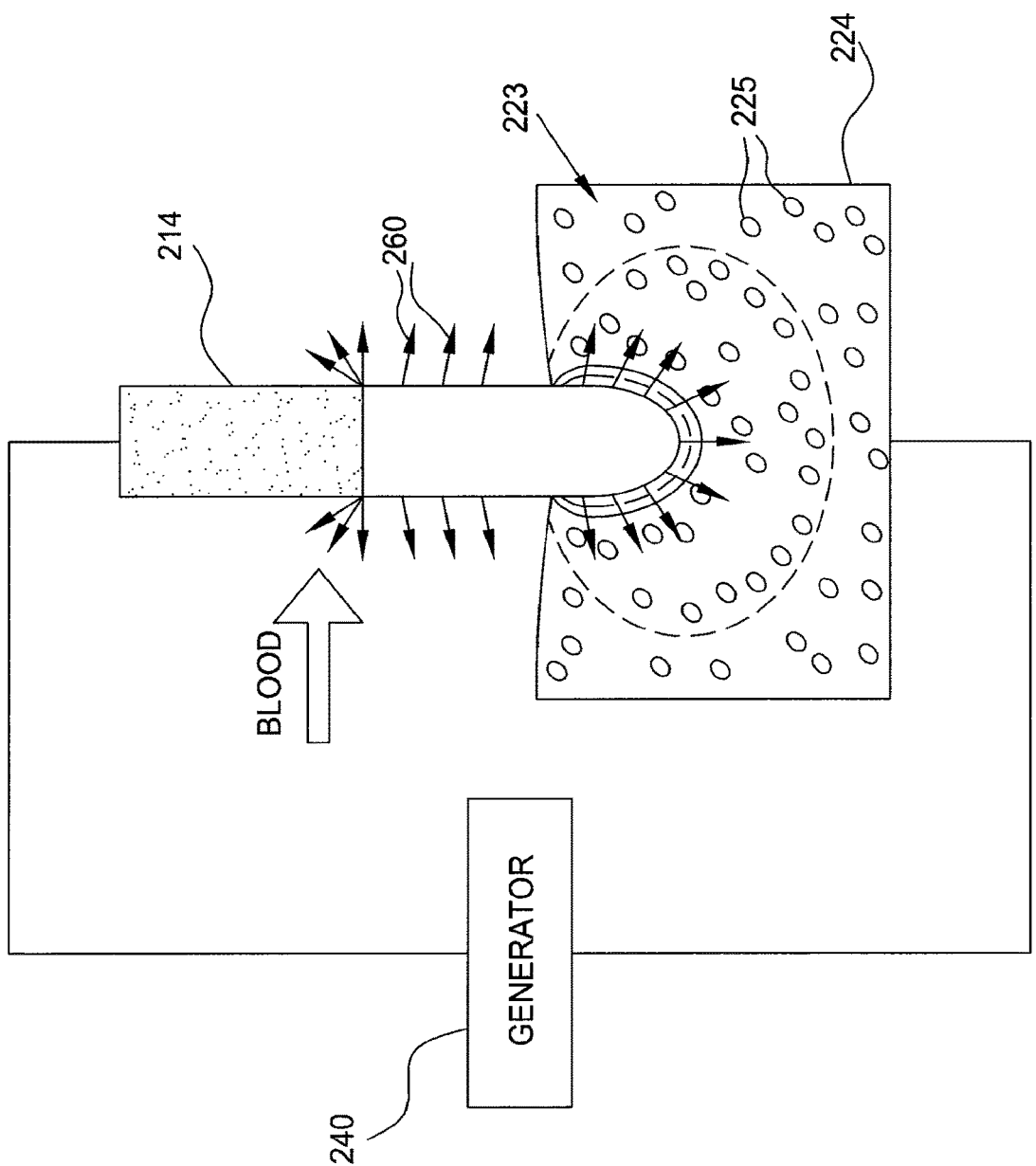
FIG. 12 is a model of the electrode catheter in contact with (or coupled to) target tissue.
Figure 12A:
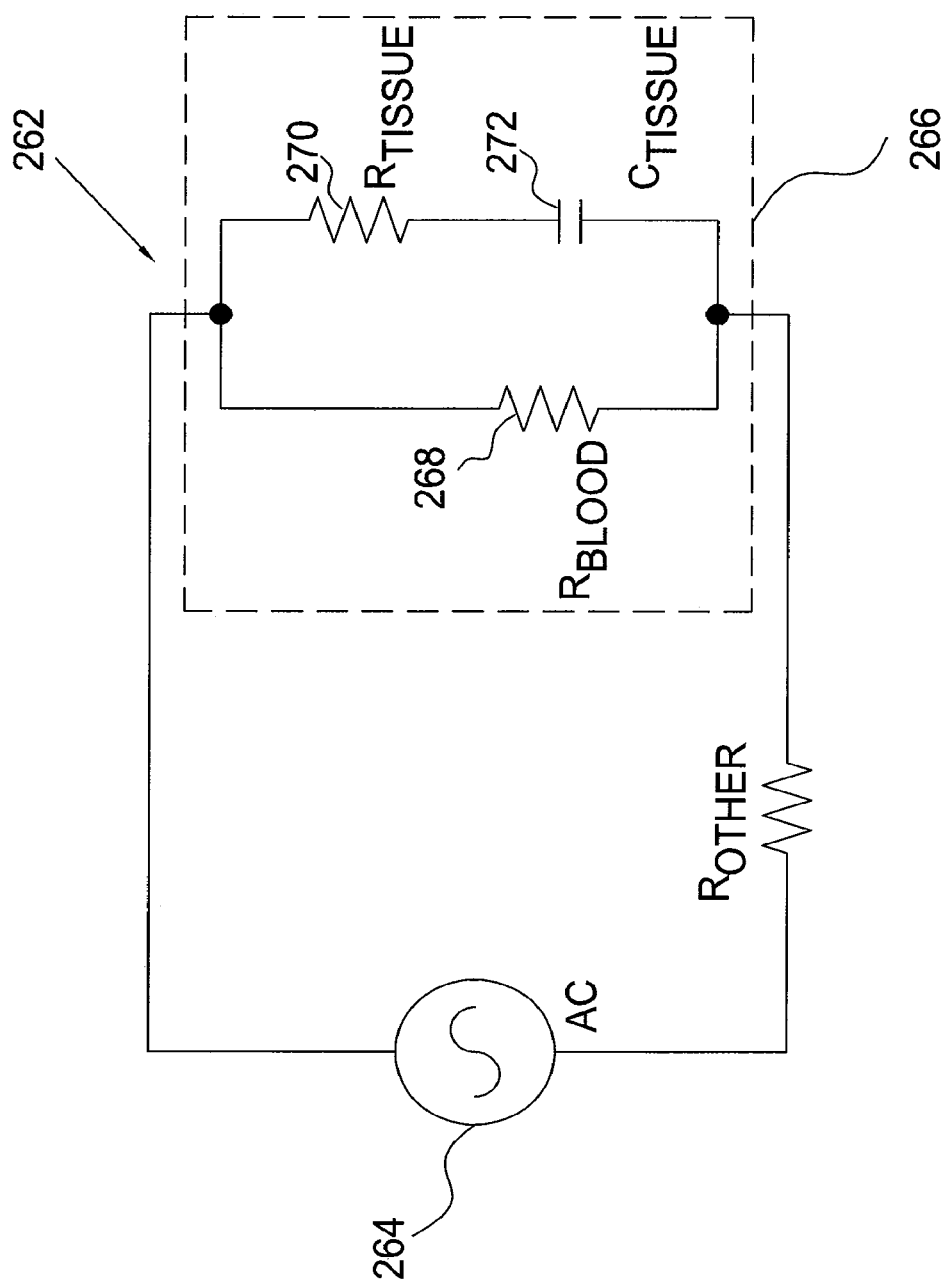
FIG. 12A is a simplified electrical circuit for the model shown in FIG. 12.

Assessing a contact or coupling condition between the electrode catheter and target tissue based on impedance measurements at the electrode-tissue interface may be better understood with reference to FIGS. 12 and 12A. FIG. 12 is a model of the electrode catheter 214 in contact with (or coupled to) target tissue 224. The electrode catheter 214 is electrically connected to the generator 240 (e.g., an RF generator). In an exemplary embodiment, the circuit may be completed through the target tissue 224, showing that current flows through the blood, myocardium, and other organs to the reference electrode, such as a grounding patch on the patient's body.

As described above, the generator 240 may be operated to generate electrical energy for emission by the electrode catheter 214. Emissions are illustrated in FIG. 12 by arrows 260. Also as described above, the generator 240 may emit a "pinging" frequency as the electrode catheter 214 approaches the target tissue 224 for assessing electrode-tissue contact or coupling. In an exemplary embodiment, this "pinging" frequency may be selected such that inductive, capacitive, and resistive effects other than those at the blood-tissue interface do not appreciably affect the impedance measurements.

In an exemplary application, capacitive effects of the blood and at the electrode-blood interface (e.g., between the metal electrode catheter and the blood) were found be minimal or even non-existent at frequencies higher than about 50 kHz. Stray inductance (e.g., due to the relatively thin catheter wires), capacitance and resistance at the electrode interface, and capacitance effects of other organs (e.g., the lungs) were also found to be minimal or even non-existent at frequencies higher than about 50 kHz. In addition, it was found that resistive effects dominate at the blood-tissue interface for frequencies below 50 kHz because the current flows into the target tissue 224 primarily via the interstitial fluid spaces 223, and the cell membranes 225 (e.g., bi-lipids or "fat") act as an insulator. However, at frequencies greater than about 50 kHz, the cell membranes 225 become conductive, and electrical current penetrates the target tissue 224 through both the interstitial fluid spaces 223 and the cell membranes 225. Accordingly, the cell membranes act as "capacitors" and the resistive effects are reduced at frequencies above about 50 kHz.

To avoid a risk of creating an ablation lesion during contact or coupling assessment, it can be desirable to use a low amount of current and power. A presently preferred range for a current of less than 1 mA is a working frequency in the approximately 50-500 kHz range. The frequency choice is mostly based on physiological aspect and engineering aspect and is within the purview of one of ordinary skill in the art. For physiological aspect, lower frequencies can introduce measurement errors due to electrode-electrolyte interface. When frequency goes higher to MHz range or above, the parasitic capacitance can become significant. It is noted, however, that the invention is not limited to use at any particular frequency or range of frequencies. The frequency may depend at least to some extent on operational considerations, such as, e.g., the application, the type of target tissue, and the type of electrical energy being used, to name only a few examples.

Assuming that a desired frequency has been selected for the particular application, the model shown in FIG. 12 may be further expressed as a simplified electrical circuit 262, as shown in FIG. 12A. In the circuit 262, the generator 240 is represented as an AC source 264. As discussed above, capacitance and resistance at the blood-tissue interface dominate impedance measurements at low frequency operation such as may be used for assessing electrode-tissue contact. Accordingly, other capacitive, inductive, and resistive effects may be ignored and the capacitive-resistive effects at the blood-tissue interface may be represented in circuit 262 by a resistor-capacitor (R-C) circuit 266. The R-C circuit 266 may include a resistor 268 representing the resistive effects of blood on impedance, in parallel with a resistor 270 and capacitor 272 representing the resistive and capacitive effects of the target tissue 224 on impedance. When the electrode catheter 214 has no or little contact with the target tissue 224, resistive effects of the blood affect the R-C circuit 266, and hence also affect the impedance measurements. As the electrode catheter 214 is moved into contact with the target tissue 224, however, the resistive and capacitive effects of the target tissue 224 affect the R-C circuit 266, and hence also affect the impedance measurements.

The effects of resistance and capacitance on impedance measurements may be better understood with reference to a definition of impedance. Impedance (Z) may be expressed as $Z=R+jX$, where R is resistance from the blood and/or tissue, j is an imaginary number indicating the term has a phase angle of +90 degrees, and X is reactance from both capacitance and inductance.

It is observed from the above equation that the magnitude of the reactance component responds to both resistive and capacitive effects of the circuit. This variation corresponds directly to the level of contact or coupling at the electrode-tissue interface, and therefore may be used to assess the electrode-tissue contact or coupling. By way of example, when the electrode catheter is operated at a frequency of 100 kHz and is primarily in contact with the blood, the impedance is purely resistive and the reactance (X) is close to 0 Ohms. When the electrode catheter contacts the target tissue, the reactance component becomes negative. As the level of contact or coupling is increased, the reactance component becomes more negative.

Alternatively, contact or coupling conditions may be determined based on the phase angle. Indeed, determining contact or coupling conditions based on the phase angle may be preferred in some applications because the phase angle is represented as a trigonometric ratio between reactance and resistance. Although the magnitude of the reactance component may be different under varying conditions (e.g., for different patients), the phase angle is a relative measurement which tends to be insensitive to external conditions.

In an exemplary embodiment, the phase angle may be determined from the impedance measurements (e.g., by the processor 250 in FIG. 11). The phase angle also corresponds directly to the level of contact or coupling at the electrode-tissue interface, and therefore may be used to assess the electrode-tissue contact or coupling. By way of example, when the electrode catheter is operated at a frequency of 100 kHz and is primarily in contact with the blood, the phase angle is close to zero (0). When the electrode catheter contacts the target tissue, the phase angle becomes negative, and the phase angle becomes more negative as the level of contact or coupling is increased. Additional details of determining the phase angle from the impedance measurement and other features of assessing electrode-tissue contact and coupling are described in U.S. Patent Application Publication Nos. 2008/0281319 and US2008/0300589, the entire disclosures of which are incorporated herein by reference.

Although impedance measurements may be used to determine the phase angle, in an alternative embodiment, the measurement circuit 242 may be implemented as a phase detection circuit to directly determine the phase angle. An exemplary phase detection circuit 280 is shown in FIG. 12. The phase detection circuit 280 is shown and described with reference to functional components. It is noted that a particular hardware configuration is not necessary for a full understanding of the invention. Implementation of the phase detection circuit 280 in digital and/or analog hardware and/or software will be readily apparent to those having ordinary skill in the electronics art after becoming familiar with the teachings herein.

The exemplary phase detection circuit 280 may include a current sensor 282 and voltage sensor 284 for measuring current and voltage at the electrode-tissue interface. The current and voltage measurements may be input to a phase comparator 286. The phase comparator 286 provides a direct current (DC) output voltage proportional to the difference in phase between the voltage and current measurements. In one embodiment, the current sensor 282 may be used to measure the ablation current. The sensor can be in series with an ablation wire. For example, a Coilcraft CST1 current sensing transformer may be placed in series with the ablation wire. Alternatively, the current wire can pass through holes of a current sensor, with or without physical connection. In addition, the voltage between the ablation electrode and the ground patch can be sensed. This voltage can be attenuated so that it can be fed into a phase sensing circuit. The phase sensing circuit then measures the current and voltage and determines the phase angle between them, which is then correlated to a coupling level. In this way, the ablation current can be used to measure the phase angle rather than injecting an additional current for the coupling sensing purpose.

Optionally, current measurements may be phase shifted by a phase shift circuit 288 to facilitate operation of the phase comparator 286 by "correcting" phase lag between the measured current and the measured voltage. Also optionally, output from the phase comparator 286 may be "corrected" by a phase adjustment circuit 290 to compensate for external factors, such as the type of grounding patch being used. A signal scaling circuit 292 may also be provided to amplify the output (e.g., from milli-volts to volts) for use by various devices (e.g., the processor 250 and display device 254 in FIG. 11).

During ablation, the measured impedance, and its component's resistance and reactance, change with tissue temperature. In such conditions, the change due to changes in tissue temperature provides a measure of lesion formation during ablation.

Figure 13:
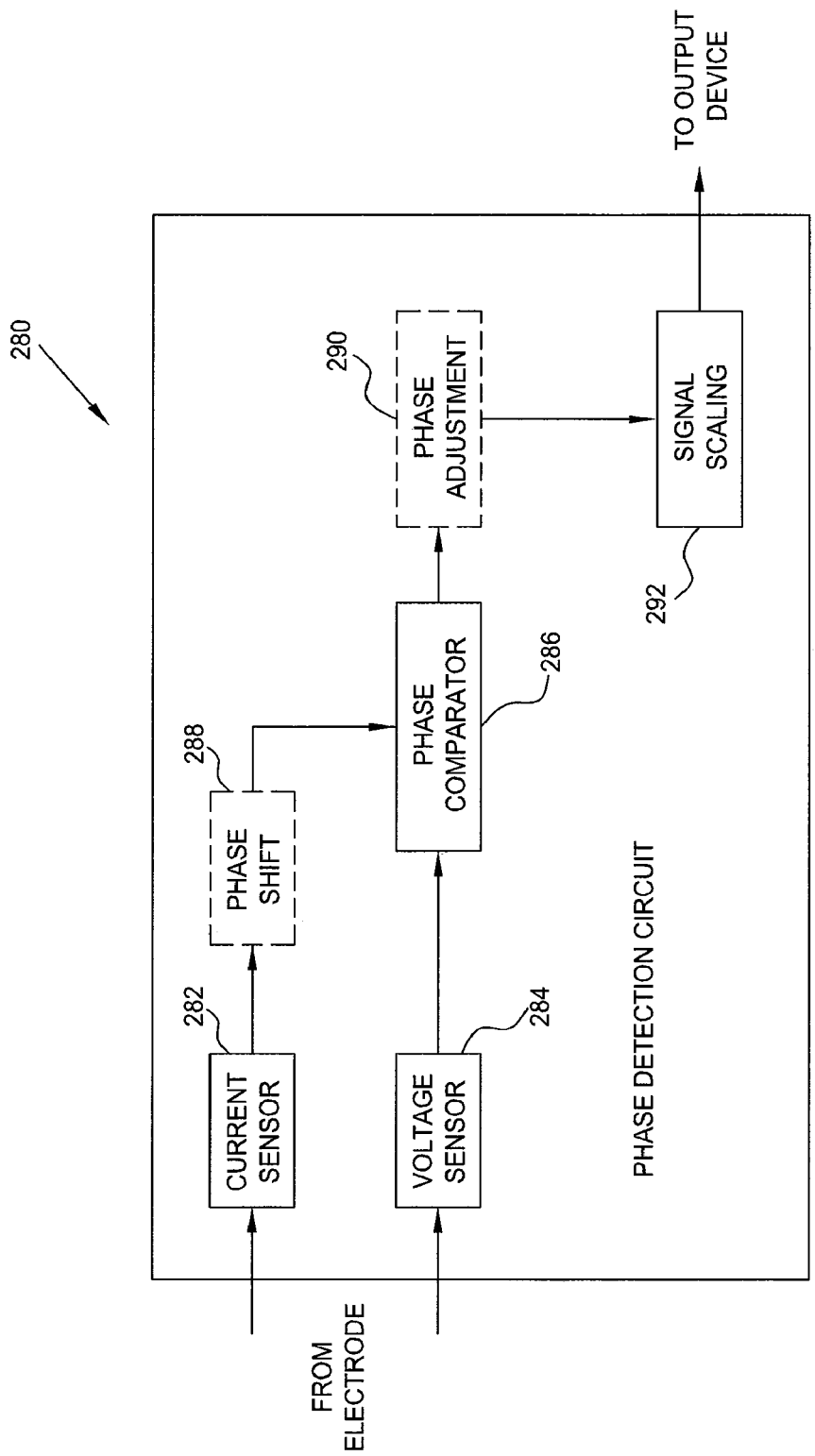
FIG. 13 is an exemplary phase detection circuit which may be implemented in a tissue ablation system for assessing electrode-tissue contact or coupling.

It is noted that the phase detection circuit 280 shown in FIG. 13 is provided as one example, and is not intended to be limiting. Other implementations may also be readily provided by those having ordinary skill in the electronics arts after becoming familiar with the teachings herein without departing from the scope of the invention.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. A catheter apparatus comprising:
   an elongated catheter body having a distal portion, a proximal end, and at least one fluid lumen extending longitudinally therein;
   a first flexible electrode segment on the distal portion of the catheter body, the first flexible electrode segment energizable to form a first ablation zone;
   a second flexible electrode segment on the distal portion of the catheter body, the second flexible electrode segment energizable to form a second ablation zone;
   an electrically nonconductive segment positioned between the first and second flexible electrode segments, wherein a length of the electrically nonconductive segment enables the first and second ablation zones to overlap and form a continuous lesion; and
   a third electrode positioned on the electrically nonconductive segment between the first and second flexible electrode segments.

2. The catheter apparatus of claim 1, wherein the electrically nonconductive segment is not as flexible as the first and second flexible electrode segments.

3. The catheter apparatus of claim 1, wherein the length of the electrically nonconductive segment is sufficiently small to provide substantially continuous flexibility across the first and second flexible electrode segments and the electrically nonconductive segment.

4. The catheter apparatus of claim 1, wherein the first and second flexible electrode segments each comprise a sidewall provided with one or more elongated stiffness reductions extending through the sidewall, the one or more elongated stiffness reductions providing flexibility in the sidewall for bending movement relative to a longitudinal axis of the catheter.

5. The catheter apparatus of claim 1, wherein the first and second flexible electrode segments are biased to stretch lengthwise.

6. The catheter of claim 1, wherein the at least one fluid lumen includes a lumen extension member extending at least partially through the first and second flexible electrode segments, the lumen extension member having a plurality of openings configured and arranged to produce a predetermined fluid flow from the lumen extension member through the first and second flexible electrode segments.

7. The catheter of claim 1, further comprising a measurement circuit coupled with the third electrode.

8. The catheter of claim 7, wherein the measurement circuit is coupled to the first and second flexible electrode segments.

9. The catheter of claim 1, wherein the third electrode is a diagnostic electrode.

10. The catheter of claim 1, wherein a ratio between a length of the first and second flexible electrode segments and a diameter of the distal portion is less than 1.7.

11. The catheter of claim 1, wherein the electrically nonconductive segment is less than 1.09 times of a diameter of the distal portion.

12. A distal portion for a catheter, the distal portion comprising:
    a first flexible electrode segment energizable to form a first ablation zone;
    a second flexible electrode segment spaced from the first flexible electrode segment and energizable to form a second ablation zone;
    an electrically nonconductive segment positioned between the first and second flexible electrode segments, wherein a length of the electrically nonconductive segment enables the first and second ablation zones to overlap and form a continuous lesion; and
    a third electrode positioned on the on the electrically nonconductive segment between the first and second flexible electrode segments.

13. The distal portion of claim 12, wherein the electrically nonconductive segment is not as flexible as the neighboring flexible electrode segments.

14. The distal portion of claim 12, wherein the first and second flexible electrode segments each comprise a sidewall provided with one or more elongated stiffness reductions extending through the sidewall, the one or more elongated stiffness reductions providing flexibility in the sidewall for bending movement relative to a longitudinal axis of the catheter, and wherein the electrically nonconductive segment is sufficiently small in length to provide substantially continuous flexibility across the flexible electrode segments and the corresponding electrically nonconductive segment.

15. The distal portion of claim 12, further comprising a fluid lumen including a lumen extension member that extends at least partially through the first and second flexible electrode segments, the lumen extension member having a plurality of openings configured and arranged to produce a predetermined fluid flow from the lumen extension member through the first and second flexible electrode segments.

16. The distal portion of claim 12, wherein the third electrode is configured to be coupled with a measurement circuit.

17. The distal portion of claim 16, wherein the first and second flexible electrode segments are configured to be coupled with the measurement circuit.

18. The distal portion of claim 12, wherein the third electrode is a diagnostic electrode.

19. The distal portion of claim 12, wherein the electrically nonconductive segment is less than 1.09 times of a diameter of the distal portion.

* * * * *